United States Patent
Davar et al.

(10) Patent No.: US 6,224,907 B1
(45) Date of Patent: May 1, 2001

(54) ANTI-ASTHMA THERAPY

(75) Inventors: Nipun Davar, Fremont; Atul Devdatt Ayer, Palo Alto; Paul Minn Hwang; Padmaja Shivanand, both of Mountain View; Brenda J. Pollock, Cupertino, all of CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/250,288

(22) Filed: Feb. 12, 1999

Related U.S. Application Data

(60) Provisional application No. 60/077,091, filed on Mar. 6, 1998.

(51) Int. Cl.[7] .............................. A61K 9/24; A61K 9/20; A61K 9/14; A61K 47/32
(52) U.S. Cl. ........................ 424/473; 424/464; 424/489; 514/772.4
(58) Field of Search .................................. 424/473, 489, 424/464; 514/772.4

(56) References Cited

U.S. PATENT DOCUMENTS

| | | | |
|---|---|---|---|
| 5,208,037 | * 5/1993 | Wright et al. | 424/473 |
| 5,681,584 | * 10/1997 | Savastano et al. | 424/473 |
| 5,702,725 | * 12/1997 | Merrill et al. | 424/472 |

FOREIGN PATENT DOCUMENTS

| | | | |
|---|---|---|---|
| 0 490 648 A1 | 6/1992 | (EP) | A61K/31/40 |
| 0 641 569 A1 | 3/1995 | (EP) | A61K/45/00 |
| WO 94/26268 | * 11/1994 | (WO) . | |
| WO 97/06787 | 2/1997 | (WO) | A61K/9/22 |

OTHER PUBLICATIONS

Qui, Y et al: Sustained–release hydrophilic matrix tablets of zileuton: . . . Journal of Controlled Release, vol. 45, No. 3, Apr. 7, 1997, p. 249–256.

Brown M.F. et al: "N–carbomoyl analogs of Zafirlukast: potent receptor antagonist of leukotriene D4" Bioorganic & Medicinal Chemistry Letters, vol. 8, No. 18, Sep. 22, 1998, p. 2451–2456 XP004138250.

* cited by examiner

*Primary Examiner*—Thurman K. Page
*Assistant Examiner*—Blessing Fubara
(74) *Attorney, Agent, or Firm*—Paul B. Simboli; Susan K. Thomas; Paul L. Sabatine

(57) ABSTRACT

A dosage form is disclosed for administering a leukatriene-receptor antagonist to a patient over time.

25 Claims, 6 Drawing Sheets

ANTI-ASTHMA THERAPY

CROSS REFERENCE TO RELATED APPLICATION

This application claims the benefits of provisional application U.S. Ser. No. 60/077,091, filed Mar. 6, 1998 under 35 U.S.C. §119(e).

FIELD OF THE INVENTION

This invention pertains to both novel and useful dosage forms comprising an antiasthma therapeutic. More particularly, the invention relates to dosage forms comprising leukotriene-receptor antagonists useful for antiasthma therapy. The invention concerns additionally therapeutic compositions comprising leukotriene-receptor antagonists, and the invention concerns a method for administering leukotriene-receptor antagonists to a patient in clinical need of antiasthma therapy.

BACKGROUND OF THE INVENTION

Medical history records asthma in the adolescent and in the adult is characterized by reversible airway obstruction, airway inflammation, and airway hyperactivity. Clinical manisfestations of asthma, such as wheezing and cough, are caused by airway obstruction, induced by reversible smooth-muscle constriction, edema and mucus secretion. Accepted medical evidence indicates asthma is an inflammatory disorder of the airways involving the production and activity of endogenous inflammatory mediators known as leukotrienes. The present treatment indicated for the management of this condition comprises the administration of a leukotriene-antagonist that produces a therapeutic benefit in the patient afflicted with asthma by inhibiting the action of leukotrienes at receptor sites on airway smooth muscles.

Leukotriene-antagonists are indicated by the medical and the pharmaceutical arts as anti-asthamatic agents for the treatment of asthma. The prior art treatment of asthma comprised administering orally a leukotriene-antagonist to a patient in need of repeated doses from once-to-four times a day. With this therapeutic profile, it is difficult to achieve continuous-prolonged therapy for the better management of asthma, as the program requires rigid compliance and it is cost ineffective.

The properties of the leukotriene-antagonists do not lend themselves to provide dosage form and drug formulations that can administer the leukotriene-antagonist at a controlled and known rate per unit time over an extended time to produce the intended therapy. For instance, the leukotriene-antagonists can be adversely affected by light, they can be insoluble in water, they can undergo a change in polymorphic form in the presence of water which results in decreased drug absorption, and they need protection from air. All of these are conditions that lead-away for sustained-release therapy in system.

It is self-evident from the above presentation a need exists for a delivery system selected from a dosage form and a drug formulation that can deliver the selected anti-asthmatic drug substantially protected from physical change and from the environment. The need exists to insure a complete dose of the anti-asthmatic drug is administered to a patient by the delivery system substantially independent of the changing environment of the gastrointestinal tract. Additionally, the need exists for a delivery system that can deliver a therapeutic dose of the selected anti-asthma drug for its intended effect and concurrently lessen the side-effects that can accompany the drug.

It will be appreciated by those in the dispensing art, that a need exists for a novel and unique sustained-release delivery system and for a method of administering an antiasthma drug in a rate-controlled dose over time. The need exists for a delivery system that can deliver a leukotriene-receptor antagonist from a sustained-release dosage form over twenty-four hours in a substantially constant dose per unit time for its beneficial therapeutic effect. Further, it will be acknowledged by those skilled in the dispensing art, that if such a novel and unique delivery system and method are made available that can administer the antiasthma drug in a sustained-release controlled dose over time, the delivery system and the method would represent an advancement and an unexpected contribution to the medical and pharmaceutical arts.

OBJECTS OF THE INVENTION

Accordingly, in view of the above presentation, it is an immediate object of this invention to provide a dosage form for delivering an anti-asthma drug from a delivery system in a sustained-release rate, which delivery system substantially overcomes the deficiencies and omissions associated with the prior art.

Another object of the present invention is to provide a dosage form for orally administering a leukotriene-receptor antagonist at a controlled-rate over an extended time indicated for treating asthma.

Another object of the invention is to make available a novel dosage form manufactured as a tablet that can administer a leukotriene-antagonist to a biological receptor to produce the desired antiasthma effect.

Another object of the invention is to provide a novel drug formulation that makes available controlled and sustained leukotriene-antagonist therapeutic activity to a patient in need of antiasthma therapy.

Another object of the present invention is to provide a dosage form manufactured as an osmotic dosage form that maintains a leukotriene antagonist in the dosage form protected from the environment including light and moisture until the leukotriene-antagonist is released from the dosage form and thereby substantially reducing and/or substantially eliminating the unwanted influences of the gastrointestinal environment of use and still provide controlled administration of the leukotriene-antagonist over a period of twenty-four hours.

Another object of the present invention is to make available a dosage form comprising a leukotriene-antagonist in an initial polymorphic form substantially-free of conversion to a different polymorphic form.

Another object of the present invention is to make available a dosage form comprising a leukotriene-antagonist in an amorphous form with a higher solubility and bioavailability protected by a formulation to substantially prevent its conversion to a crystalline form with decreased solubility.

Another object of the invention is to make available a dosage form adapted as a tablet that administers a leukotriene-antagonist at a controlled-rate over a sustained release time of twenty-four hours for its therapeutic benefit accompanied by a lessening of possible unwanted side-effects.

Another object of the present invention is to provide a dosage form that contains initially an amorphous leukotriene-antagonist protected by a light-resistant semi-permeable polymeric wall from light and can be administered in a dose in a rate controlled by the dosage form.

Another object of the invention is to provide a dosage form adapted for oral administration of a leukotriene-antagonist in a single drug composition that operates with the dosage form for the controlled administration of the leukotriene-antagonist to a patient.

Another object of the invention is to provide a dosage form sized for oral administration comprising a leukotriene-antagonist in a first drug composition in contacting layered arrangement with a second force generating second push composition that operate in combination for the controlled administration of the leukotriene-antagonist to a patient.

Another object of the present invention is to provide a complete pharmaceutical leukotriene-antagonist regimen comprising a composition comprising a leukotriene-antagonist that can be dispensed from the composition, the use of which requires intervention only for initiation of the regimen.

Another object of the present invention is to provide a complete pharmaceutical leukotriene-antagonist regimen comprising a dosage form that dispenses the leukotriene-antagonist over time, the use of which requires intervention only for the initiation and possibly for termination of the therapeutic regimen.

Another object of the invention is to provide a method for treating asthma by orally administering a leukotriene-antagonist from a delivery device in a rate-controlled amount per unit time over twenty-four hours to a warm-blooded animal in need of antiasthma therapy.

Other objects, features and advantages of this invention will be more apparent to those versed in the delivery arts from the following detailed specification, taken in conjunction with the accompanying claims.

BRIEF DESCRIPTION OF DRAWINGS

In the drawing figures, which are not drawn to scale, but are set forth to illustrate various embodiments of the invention, the drawing figures are as follows.

Drawing

Drawing

Drawing

Drawing

Drawing

Figure 1:
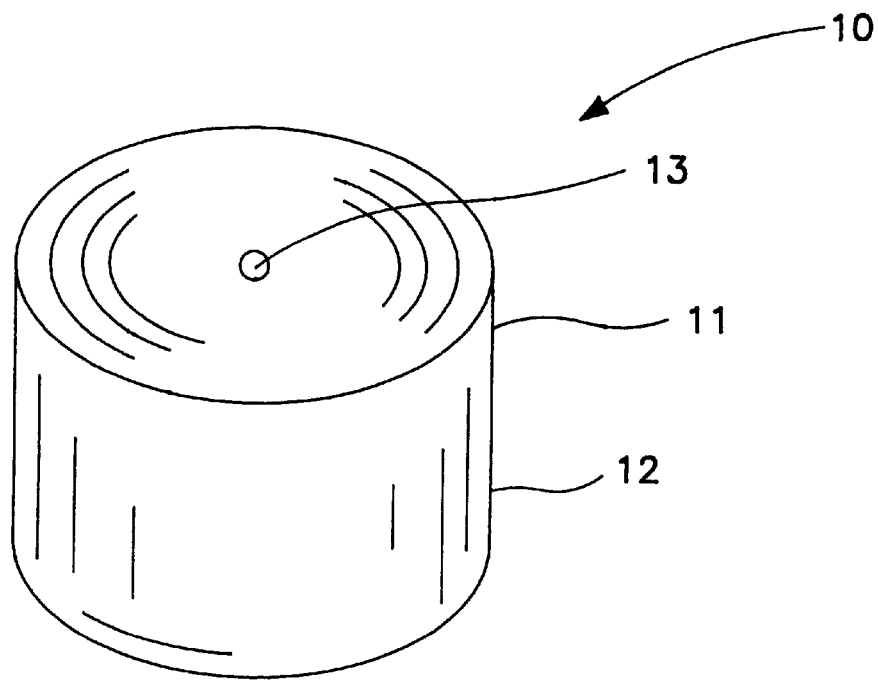
FIG. 1 is a general view of a dosage form provided by this invention, designed and shaped for the oral administration of a leukotriene-antagonist for the treatment of asthma at a controlled rate to a human patient in need of anti-asthma therapy.

Other objects, features, and advantages of the invention will be more apparent to those versed in the dispensing art from the accompanying specification, taken in conjunction with the drawing figures and the claims.

DETAILED DESCRIPTION OF DRAWINGS

Turning now to the drawing figures in detail, which drawing figures are examples of dosage forms provided by this invention, and which examples are not to be construed as limiting, one example of a dosage form is seen in drawing FIG. 1. In drawing FIG. 1, a dosage form 10 is seen comprised of a body member 11, which body member 11 comprises wall 12. Wall 12 is an exterior wall and it surrounds and forms an internal area, not seen in drawing FIG. 1. Drawing FIG. 1 comprises at least one exit 13 that connects the exterior of drawing FIG. 1 with the interior of dosage form 10.

The dosage form 10 of drawing FIG. 1 illustrates a controlled-release dosage form that delivers a leukotriene-antagonist over a sustained-release time. The phrase controlled-release denotes the dosage form controls the delivery of a leukotriene-antagonist from the dosage form over a sustained-release time of ½ up to 24 hours. The dosage form provided by this invention is useful for maintaining therapeutic leukotriene-antagonist levels in blood, including blood plasma. The dosage form, as seen in drawing FIG. 1, embraces the shape of a dosage form tablet, and it could embrace the shape of a dosage form capsule and other dosage forms. The sustained-release, continuous time of delivery for the dosage form denotes a delivery time greater than conventional, non-controlled tablets and non-controlled capsules, both of which exhibit dose-dumping of their drug.

Figure 2:
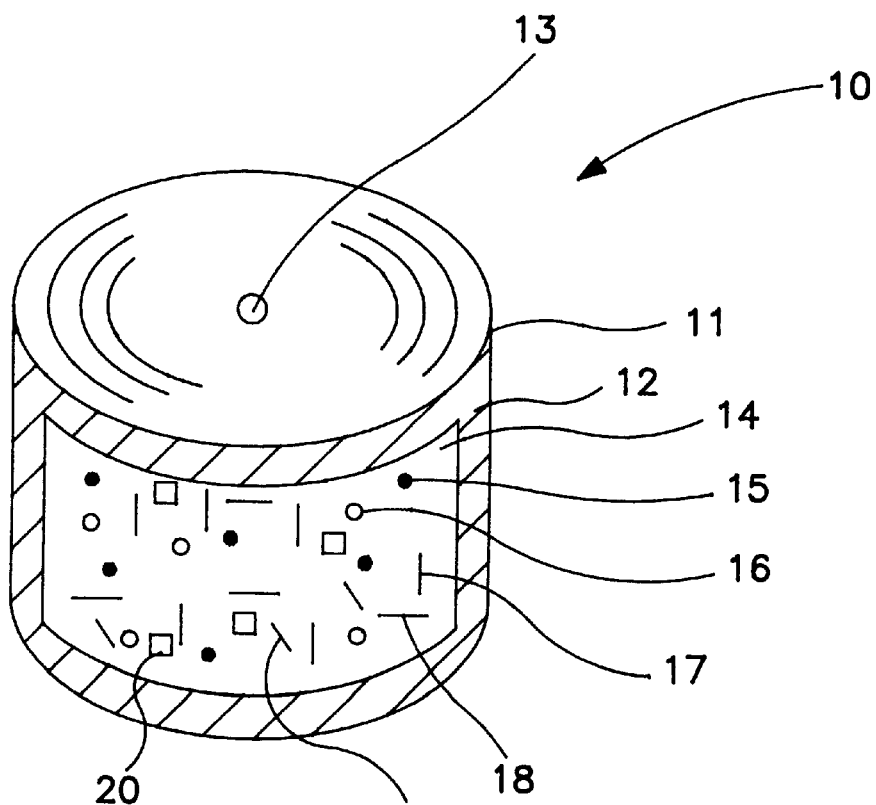
FIG. 2 is an opened view of drawing FIG. 1, depicting a dosage form of the invention comprising an internal pharmaceutically acceptable composition comprising a leukotriene-antagonist indicated for the management of asthma.

In drawing FIG. 2, dosage form 10 is seen in opened-section with a section of wall 12 removed for illustrating the internal area 14 of dosage form 10. The internal area 14 can be described as a compartment too. In drawing FIG. 2, dosage form 10 comprises body 11, wall 12, exit passageway 13, and internal compartment 14. Wall 12, which surrounds and defines internal compartment 14, comprises totally or in at least a part a semipermeable composition. The semipermeable composition is permeable to the passage of an exterior fluid, such as an aqueous fluid, and wall 12 is permeable to the passage of a biological fluid present in the gastrointestinal tract. Wall 12 is nontoxic and it is impermeable to the passage of leukotriene-receptor antagonist 15, represented by dots, present in compartment 14. Wall 12 is inert, and it maintains its physical and chemical integrity during the dispensing life of leukotriene-antagonist 15. The phrase "maintains its physical and chemical integrity" means wall 12 does not lose its structure and it does not undergo chemical change during the dispensing of leukotriene-antagonist 15.

Wall 12 comprises a composition that does not adversely affect an animal, a human, or components of the dosage form. Compositions for forming wall 12 are, in one embodiment, comprised of a member selected from the group consisting of a cellulose ester polymer, a cellulose ether polymer and a cellulose ester-ether polymer. These cellulosic polymers have a degree of substitution, DS on the anhydroglucose unit, from greater than 0 up to 3 inclusive. By "degree of substitution" is meant the average number of hydroxyl groups originally present on the anhydroglucose unit comprising the cellulose polymer that are replaced by a substituting group. Representative wall 12 polymers comprise a member selected from the group consisting of cellulose acylate, cellulose diacylate, cellulose triacylate, cellulose acetate, cellulose diacetate, cellulose triacetate, mono-, di- and tricellulose alkanylates; mono-, di and tricellulose aroylates; mono-, di- and tricellulose alkenylates; and mono-, di- and tricellulose alkinylates. Exemplary polymers include cellulose acetate having a DS of up to 1 and an acetyl content of up to 21%; cellulose acetate having a DS of 1 to 2 and an acetyl content of 21 to 35%; cellulose acetate having a DS of 2 to 3 and an acetyl content of 35 to 44.8%, and the like. More specific cellulosic polymers comprise cellulose propionate having a DS of 1.8, a propyl content of 39.2 to 45% and a hydroxyl content of 2.8 to 5.4; cellulose acetate butyrate having a DS of 1.8, an acetyl content of 13 to 15% and a butyryl content of 34 to 39%; cellulose acetate butyrate having an acetyl content of 2 to 29%, a butyryl content of 17 to 53% and a hydroxy content of 0.5 to 4.7; cellulose triacylates having a DS of 2.9 to 3, such as cellulose trivalerate, cellulose trilaurate, cellulose tripalmitate, cellulose trisuccinate and cellulose trioctanoate; celluloses diaceylate having a DS of 2.2 to 2.6, such as cellulose disuccinate, dipalmitate, cellulose acetate butyrate and cellulose acetate propionate.

Additional semipermeable polymers comprise acetaldehyde dimethylcellulose acetate; cellulose acetate ethylcarbamate; cellulose acetate methylcarbamate; cellulose diacetate propylcarbamate; cellulose acetate diethylaminoacetate; semipermeable polyamide; semipermeable polyurethane; semipermeable sulfonated polystyrene; semipermeable crossliked selective polymer formed by the coprecipitation of a polyanion and polycation, as disclosed in U.S. Pat. Nos. 3,173,876, 3,276,586, 3,541,005, 3,541,006 and 3,546,876; semipermeable polymers as disclosed by Loeb and Sourirajan in U.S. Pat. No. 3,133,132; semipermeable, lightly crosslinked polystyrenes; semipermeable crosslinked poly(sodium styrene sulfonate); semipermeable cross-linked poly(vinylbenzytrimethyl ammonium chloride); and semipermeable polymers possessing a fluid permeability of $2.5 \times 10^{-8}$ to $5 \times 10^{-3}$ ($cm^2$/hr·atm), expressed per atmosphere of hydrostatic or osmotic pressure difference across the semipermeable wall. The polymers are known to the polymer art in U.S. Pat. Nos. 3,845,770; 3,916,899 and 4,160,020; and in *Handbook of Common Polymers*, Scott, J. R. and W. J. Roff, 1971, CRC Press, Cleveland, Ohio. Wall 12 can comprise 100 wt % of a cellulosic polymer, or the wall can comprise a cellulosic polymer and polyoxyethylene-polyoxypropylene glycol copolymer. When wall 12 comprises both the cellulosic polymer and the copolymer, the wall comprises 75 to 85 wt % cellulosic polymer, and 25 to 15 wt % polyoxy-ethylene-polyoxypropylene glycol copolymer. The copolymers are nonionic with an average molecular weight of 7,000 to 14,600.

The dosage amount of a leukotriene-receptor antagonist 15 in compartment 14 of dosage form 10 is 2 mg to 500 mg. The leukotriene-antagonist can be present in doses of, for example, 5, 20, 40, 60, 80, 100, 225, 350, or 400 mg. The leukotriene-antagonist dose can be selectively delivered at a rate of 0.08 mg/hr up to 20 mg/hr (milligram/hour), to provide proportional to the administered dose a plasma concentration of 0.01 µg/ml to 75 µg/ml (micrograms/milliliter). Representative of leukotriene-receptor antagonist that can be administered according to the invention comprise acitazanolast, iralukast, montelukast, praniukast, velukast, zafirlukast, and zilenton. The leukotriene-antagonist can be in an amorphous form, a crystalline monhydrate form, or in an anhydrous form. This invention provides a formulation for administering a leukotriene-antagonist in these forms including the initial form that does not change to a different form. For example, the amorphous form presently is preferred for zafirlukast as it possesses increased bioavailability than the anhydrous crystalline or crystalline monohydrate forms, and the formulations of this invention comprising zafirlukast substantially prevent its conversion into the crystalline forms. The formulation provided by this invention maintained zaferlukast in the selected form substantially-free of conversion to a different form during dosage form tablet manufacture, on storage, and on administration. The term "substantial" denotes more than ninety-five percent of the selected form remains in that form.

A solubility enhancing agent 16, identified by circles, is present in compartment 14 for increasing the solubility and concomitantly the concentration of a leukotrieneantagonist, for example, zafirlukast in solution. The solubility enhancing agent maintains a high pH environment for keeping the zafirlukast in solution. The enhancing agents as used for this invention increase the solubility of zafirlukast at least two fold. Zafirlukast is poorly soluble in aqueous fluid and a need exists for increasing its solubility for correspondingly increasing the dose of zafirlukast that can be delivered without resulting in an unacceptably large delivery composition, and/or dosage form, or conversion to a different form. The solubility enhancing agents useful for this invention comprises a method selected from the group consisting of tromethamine also known as; tris (hydroxymethyl)aminomethane; diethanolamine; glycineamide; triethanolamine; N-[tris-(hydroxymethyl) methyl] glycine; sodium acetate; sodium lactate; sodium glycocholate; sodium propionate; sodium butyrate; sodium glycoholate; glycocholate sodium phosphate; potassium phosphate monobasic; potassium biphthalate; boric acid; sodium borate; and sodium phosphate. The solubility enhancing agents function as an alkalinizing agent to maintain an alkaline environment. The amount of solubility enhancing agent present in composition or dosage form is 5 to 30 wt %, or 10 to 50 mg.

Compartment 14 contains a pharmaceutically acceptable osmopolymer 17 carrier, represented by vertical dashes, homogenously blended with the leukotriene-antagonist 15. The osmopolymer 17 useful for this purpose is compatible with leukotriene-antagonist. The osmopolymer aids in transporting a leukotriene-antagonist in a known dose to a patient. The osmopolymers comprise a member selected from the group consisting of a polyalkylene oxide possessing a 75,000 to 600,000 weight-average molecular weight, and a carboxyalkylcellulose possessing a 30,000 to 300,000 weight-average molecular weight. Representative of polyalkylene oxides comprise a polyethylene oxide of 100,000 molecular weight; a polyethylene oxide of 200,000 molecular weight; a polyethylene oxide of 300,000 molecular weight; a polypropylene oxide of 400,000 molecular weight and a polypropylene oxide of 600,000 molecular weight. Representative of carboxyalkylcellulose is alkali carboxyalkylcellulose, including sodium and potassium carboxymethylcellulose of 30,000 molecular weight, sodium carboxymethylcellulose of 40,000 molecular weight, sodium carboxymethylcellulose of 75,000 molecular weight and sodium carboxymethylcellulose of 90,000 molecular weight. The composition comprising the leukotriene-antagonist contains 20 to 300 mg of osmopolymer 17, or 10 to 70 wt %.

The drug formulation comprises 15 to 40 wt %, or 40 to 75 mg of a compatible binder, represented by horizontal dashes 18. The binder 18 is represented by a member selected from the group consisting of a 2,500 to 3,000,000 viscosity-average molecular weight polyvinylpyrrolidone polymer and copolymer thereof, such as a copolymer of polyvinylpyrrolidone with vinyl acetate, copolymer of polyvinyl with vinyl alcohol, copolymer of polyvinylpyrrolidone with vinyl chloride, copolymer of polyvinylpyrrolidone with vinyl fluoride, copolymer of polyvinylpyrrolidone with vinyl butyrate, copolymer of polyvinylpyrrolidone with vinyl laurate, and a copolymer of polyvinylpyrrolidone with vinyl stearate. The binder can be selected from a hydroxypropylalkylcellulose of 9,200 to 225,000 number-average molecular weight selected from the group consisting of hydroxypropylmethylcellulose, hydroxypropylethylcellulose, hydroxypropylbutylcellulose, and hydroxypropylpentylcellulose. The binder imports cohesive qualities to the ingredients in the composition.

The leukotriene-antagonists composition comprises 0.05 to 3.0 wt % or 0.1 to 15 mg of a lubricant, represented by slanted dashes 19. The lubricants are used during manufacture to provide an antifriction surfaces. The lubricants comprise a member selected from the group consisting of sodium stearate, magnesium stearate, stearic acid, calcium stearate, oleic acid, potassium oleate, caprylic acid, glycerol monostearate, glyceryl palmitostearate, hydrogenated castor oil, hydrogenated vegetable oil, sodium benzoate, sodium stearyl fumarate, talc, zinc stearate, zinc oleate, and zinc palmitate.

The leukotrieneantagonist composition comprises 0 to 5.0 wt %, or 0 to 20 mg of colloidal silicon dioxide. The colloidal silicon dioxide provides flow characteristics to improve the flow and static properties of ingredients used in granulating and tableting the composition for use as the composition or in a dosage form.

The leukotrieneantagonists composition comprises 0 to 75 mg, or 0 to 30 wt % of an osmagent 20, represented by squares, selected from the group consisting of magnesium sulfate, magnesium chloride, sodium chloride, potassium chloride, lithium chloride, postassium sulfate, sodium sulfate, mannitol, sorbitol, inositol, glucitol, urea, sucrose, glucose, fructose and lactose. The osmagents, also known as osmotic agents, osmotically effective compounds and osmotic solutes, and they exhibit an osmotic pressure gradient across semipermeable wall 12 of 2.5 to 500 atmospheres. The osmagents imbibe an aqueous fluid through wall 12 for hydro-osmotically delivering a leukotriene-antagonist 15 from dosage form 10.

Figure 3:
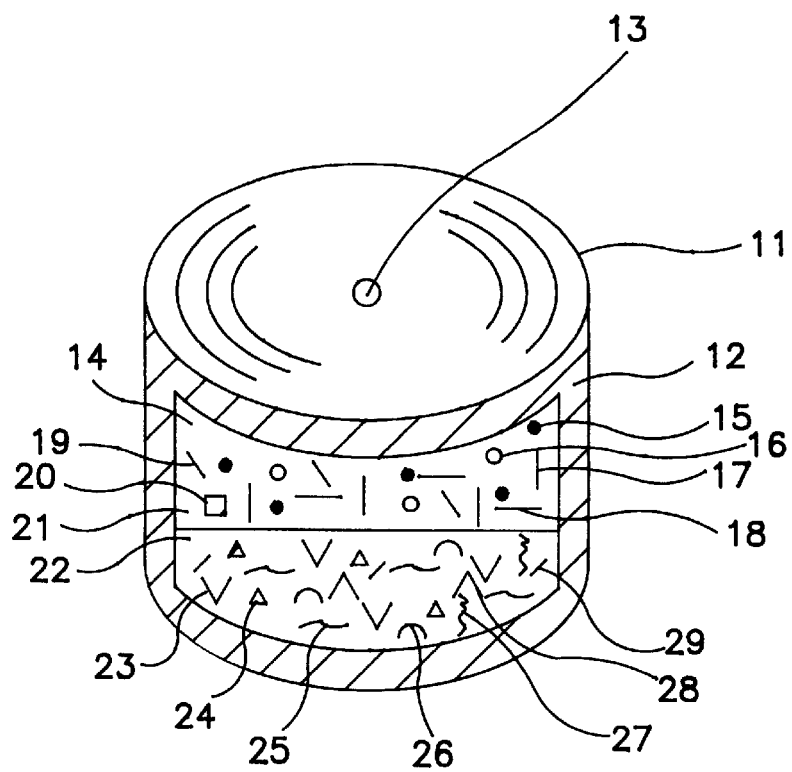
FIG. 3 is an opened view of drawing FIG. 1 illustrating a dosage form comprising a pharmaceutical leukotriene-antagonist composition and a separate, contacting composition comprising means for pushing the pharmaceutical leukotriene-antagonist from the dosage form.

In drawing FIG. 3, dosage form 10 is seen in opened view for illustrating internal compartment 14. Internal compartment 14 comprises the leukotriene-antagonist described in detail in drawing FIG. 2. The leukotriene-antagonist composition is identified in drawing FIG. 3 as leukotriene-antagonist layer 21. Dosage form 10 in compartment 14 of drawing FIG. 3 comprises an expandable composition 22, also identified as expandable layer 22. Expandable layer 22 pushes and cooperates with leukotriene-antagonist layer 21 for delivering a leukotriene-antagonist 15 from dosage form 10.

Expandable layer 22 comprises 25 to 400 mg, or 20 to 70 wt % of an expandable osmopolymer 23, represented by v. The osmopolymer 23 comprises a member selected from the group consisting of a polyalkylene oxide of 1,000,000 to 10,000,000 weight-average molecular weight. The osmopolymer 23 in expandable layer 22 possess a higher molecular weight than osmopolymer 17 in layer 21. Representative of the polyalkylene oxides are polyethylene oxide of 1,000,000 molecular weight, a polyethylene oxide of 2,000,000 molecular weight, a polyethylene of 5,000,000 molecular weight, a polyethylene oxide of 7,500,000 molecular weight, a polypropylene oxide of 3,000,000 molecular weight, and a polypropylene oxide of 7,800,000 molecular weight. The osmopolymer 23 comprises an expandable carboxyalkylcellulose comprising the alkali sodium and potassium carboxyalkylcellulose including sodium carboxymethylcellulose of 300,000 molecular weight, sodium carboxymethylcellulose of 1,250,000 molecular weight, sodium carboxymethylcellulose of 3,250, 000 molecular weight, potassium carboxymethylcellulose of 2,500,000 and potassium carboxyethylcellulose of 3,175,000 molecular weight. The osmopolymers present 23 in layer 22 exhibit an osmotic pressure gradient across semipermeable wall 12; they imbibe fluid into compartment 14; and they thereby expand and push the leukotriene-antagonist 15 from the dosage form.

Expandable layer 22 comprises 20 to 70 wt %, or 5 to 100 mg of an osmotically active solute 24, represented by a triangle. The osmotically active solutes are known as osmotically effective compounds, and as osmagents too. The osmotically effective solutes contribute to the delivery kinetics of leukotriene-antagonist 15, by imbibing in fluid for osmopolymer 23 and generating osmotic pressure whereby layer 22 expands and pushes against layer 21. Representative of osmotically active solute 24 is a member selected from the group consisting of sodium chloride, urea, sorbitol, potassium chloride, magnesium sulfate, lithium phosphate, lithium chloride, sodium phosphate, potassium sulfate, sodium sulfate, and potassium phosphate.

Expandable layer 22 comprises a hydroxypropylalkylcellulose 25, represented by a wavy line, in the amount of 1 to 15 wt %, or 1 to 20 mg. The hydroxypropylalkylcellulose possesses a 9,000 to 400,000 number-average molecular weight and it is used as a suspending agent and as a tablet binder. The hydroxypropylalkylcellulose comprise a member selected from the group consisting of hydroxypropylmethylcellulose, hydroxypropylethylcellulose, hydroxypropylisopropylcellulose, hydroxypropylbutylcellulose, and hydroxypropylpentylcellulose.

Expandable layer 22 comprises a hydroxyalkylcellulose 26, represented by a half-circle. The concentration of hydroxyalkylcellulose in layer 22 is 0 to 10 wt %, presently 2 to 10 wt % or 3 to 10 mg. The hydroxyalkylcellulose is used for its stabilizing and binding properties in tablet formation. The hydroxyalkylcellulose possesses a viscosity-number molecular weight of 7,500 to 1,150,000 selected from the group consisting of hydroxyethylcellulose, hydroxybutylcellulose, hydroxypropylcellulose and hydroxybutylcellulose.

Expandable layer 22 comprises 0 to 3 wt %, or 0 to 5 mg of a nontoxic colorant, 27 represented by a vertical wavy line. Colorant 26 includes the Food and Drug Administration colorants such as FD&C No. 1 blue, FD&C No. 3 green, FD&C No. 4 red, FD&C No. 40 red, FD&C No. 5 yellow, red ferric oxide, tartrazine, erythrosine, carmel, lake red, and indigotine. A lubricant 28 is formulated into expandable layer in 0 to 3 wt %, or 0 to 4 mg. The lubricants include the lubricants set forth previously. Expandable layer 22 comprises 0.1 to 1 wt %, or 0.1 to 1.5 mg of colloidal silicon dioxide 29.

Figure 4:
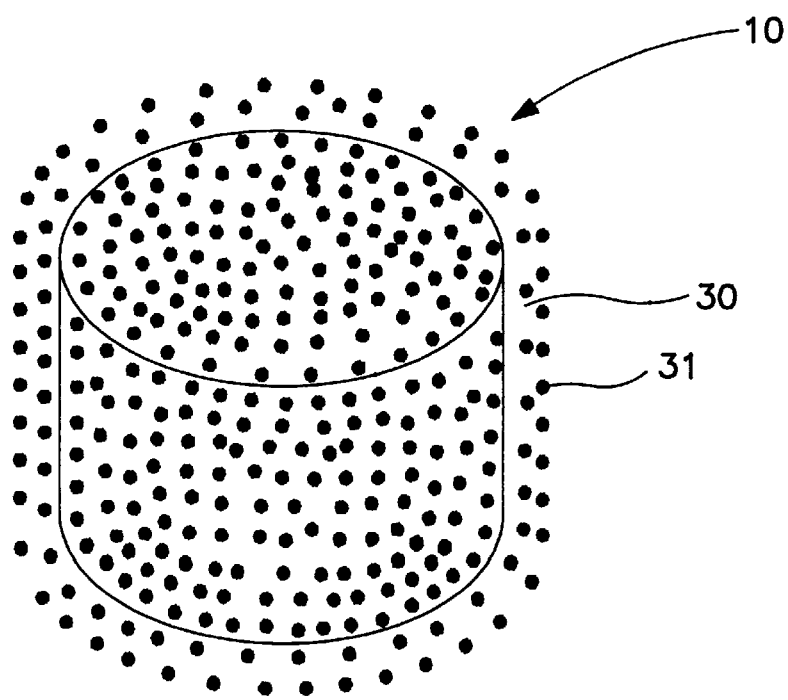
FIG. 4 is a view of a dosage form provided by this invention, which dosage form comprises an instant-release overcoat on the exterior of the dosage form, and comprises an immediate dose of a leukotrieneant-agonist.

Dosage form 10 as seen in drawing FIG. 4 depicts another manufacture provided by the invention. Dosage form 10 comprises an overcoat 30 on the outer surface of dosage form 10. The overcoat 30 is a therapeutic composition comprising 0 to 50 mg of leukotriene-antagonist 31 and a pharmaceutically acceptable carrier selected from the group consisting of alkylcellulose, hydroxyalkylcellulose and hydroxypropylalkylcellulose. Representative of the pharmaceutically acceptable carrier include methylcellulose, hydroxyethylcellulose, hydroxypropylcellulose, hydroxypropylmethylcellulose, hydroxypropylethylcellulose and hydroxypropylbutylcellulose. Overcoat 30 provides therapy immediately as overcoat 30 dissolves or undergoes dissolution in the presence of gastrointestinal fluid, and concurrently therewith delivers leukotrieneant-agonist on entrance into the gastrointestinal tract for immediate leukotriene-antagonist therapy.

Dosage form 10, manufactured as an osmotically controlled-release dosage form, comprises at least one passageway 13. The phrase "controlled-release" as used herein indicates that control is exercised over both the duration and the profile of the leukotriene-antagonist release pattern.

The expression "passageway" as used for the purpose of this invention includes aperture; orifice; bore; pore; porous element through which leukotriene-antagonist drug 15 can be pumped, diffuse or migrate through a fiber; capillary tube; porous overlay; porous insert; microporous member and porous composition. The passageway includes also a compound that erodes or is leached from wall 12 in the fluid environment of use to produce at least one passageway. Representative compounds for forming a passageway include erodible poly(glycolic) acid, or poly(lactic) acid in the wall; a polyoxyethylene-polyoxypropylene glycol copolymer; a gelatinous filament; a water-removable poly (vinyl alcohol); leachable compounds, such as fluid-removable pore-forming polysaccharides, acids, salts or oxides. A passageway can be formed by leaching a compound from the wall, such as sorbitol, sucrose, lactose, maltose or fructose, to form a controlled-release dimensional pore-passageway. The passageway can have any shape, such as round, triangular, square and elliptical, for assisting in the controlled-metered release of zafirlukast from the dosage form. The dosage form can be manufactured with one or more passageways in spaced-apart relation on one or more surfaces of the dosage form. A passageway and equipment for forming a passageway are disclosed in U.S. Pat. Nos. 3,845,770 and 3,916,899 by Theeuwes and Higuchi; in U.S. Pat. No. 4,063,064 by Saunders, et al. and in U.S. Pat. No. 4,088,864 by Theeuwes, et al. Passageways comprising controlled-release dimensions sized, shaped and adapted as a releasing-pore formed by aqueous leaching to provide a releasing-pore of controlled-release rate are disclosed in U.S. Pat. Nos. 4,200,098 and 4,285,987 by Ayer and Theeuwes.

PROCESS FOR PROVIDING THE INVENTION

Wall 12 of dosage form 10 is manufactured in one process, comprising an air suspension process. This process consists in suspending and tumbling a compressed drug core, comprising a single-layered core or a bilayered core, in a current of air and wall-forming composition until a wall is applied to the single-layered core (or tablet), or the bilayered core, (or tablet). The air suspension procedure is described in U.S. Pat. No. 2,799,241; *J. Amer Pharm Assoc.*, Vol. 48, pp. 451–454 (1959); and *ibid.*, Vol. 49, pp. 82–84 (1960). Dosage form 10 can be coated also with a wall-forming composition in a Wurster® air suspension coater using 100% acetone, or methylene dichloride-methanol cosolvent, for example, 80:20 wt:wt, or ethanol-water, or acetone-water cosolvent, or a 95:5 wt:wt using 2.5 to 4% solids. An Aeromatic® air suspension coater using a methylene dichloride-methanol cosolvent, for example, 80:20 wt:wt, can be used for appying the wall. Other wall-forming techniques, such as a pan-coating system, wherein wall-forming compositions are deposited by successive spraying of the composition to provide a wall surrounding a compartment, accompanied by tumbling in a rotating pan can be used to provide the dosage form. Finally, the wall coated cores (or tablets) are dried in a forced-air oven at 30 to 50° C. for up to a week to free the dosage form of solvent. Generally, the walls formed by these techniques have a thickness of 1 to 30 mils (0.0254 to 0.762 mm).

Dosage form 10 of the invention is manufactured by general manufacturing techniques. For example, in one manufacture the drug and other core-forming, or tablet-forming ingredients comprising a single drug layer or bilayer core with drug facing the exit means 13 are blended and pressed into a solid layer, or a solid bilayer. The drug and other ingredients can be dry-blended or blended with a solvent and mixed into a solid or semisolid formed by conventional methods such as ball-milling, calendaring, fluid bed granulating, stirring, roll-milling or churning, roller compacting, and then pressed into a preselected shape. The layer possesses dimensions that correspond to the internal dimensions of the area the layer occupies in the dosage form, and in a bilayer it also possesses dimensions corresponding to the second layer for forming a contacting arrangement therewith. In a bilayered core, the push layer is placed in contact with the drug layer. The push layer is manufactured using similar techniques as used for manufacturing the drug layer. The layering of the drug layer and the push layer can be fabricated by conventional press-layering techniques. Finally, a single layer of the two-layer compartment-forming members are surrounded and coated with an exterior wall or with an interior and exterior wall. A passageway is laser or mechanically drilled through the wall to contact the drug layer. When the passageway is formed by a laser, the dosage form is optically-oriented automatically by the laser equipment for forming the passageway on the preselected surface for forming the passageway.

In another manufacture, dosage form 10 is manufactured by the wet granulation technique. Granulation is a process of size enlargement whereby small particles are gathered into larger aggregates or granules, as reported in *Encyclopedia of Pharmaceutical Technology*, Vol. 7, pp. 121–160, 1993. In the wet granulation technique, for example, the drug and the ingredients comprising the drug-forming layer or the drug-expandable layers are blended using a solvent, such as ethyl alcohol-water 98:2 v:v (volume:volume) as the granulation fluid. Other granulating fluid, such as denatured alcohol 100%, can be used for this purpose. The ingredients forming the drug core or layers are individually passed through a mesh screen, such as an U.S. Sieve Series screen, and then thoroughly blended in a mixer. Other ingredients comprising the layer or layers are dissolved in a portion of the granulation fluid, such as the cosolvent described above. Then, the latter-prepared wet blend is added slowly to the drug blend with continual mixing in the blender. The granulating fluid is added until a wet blend is produced, which wet mass is then forced through a mesh screen onto oven trays. The blend is dried for 18 to 24 hours at 30 to 50° C. The dry granules are sized then with a mesh screen. Next, a lubricant is passed through a screen and added to the dry screened granule blend. The granulation is placed in a blender and blended for 1 to 15 minutes.

An expandable-push layer is made by the same wet granulation procedure, which consists in suspending and tumbling the ingredients in a current of air. Then, the layers are surrounded with a wall-forming composition. The delivery system provided by this invention are generally manufactured in a controlled humidity environment consisting of a relative humidity of less than 40%. The air suspension procedure is described in U.S. Pat. No. 2,799,241; *J. Amer Pharm. Assoc.*, Vol. 48, pp. 451–454 (1979); and *ibid.*, Vol. 49, pp. 82–84 (1960). Other standard manufacturing procedures are described in *Modem Plastics Encyclopedia*, Vol. 46, pp. 62–70 (1969); and in *Pharmaceutical Sciences*, Remington, 14th Ed., pp. 1626–1648 (1970) Mack Publishing Co. Easton, Pa.

Exemplary solvents suitable for manufacturing the wall, a single layer and a bilayer include inert inorganic and organic solvents. The solvents include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone, alcohol, methanol, ethanol, isopropyl alcohol, butyl alcohol, methyl acetate, ethyl acetate, isopropyl acetate, n-butyl acetate, methyl ethyl ketone, methyl ethyl petone, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclooctane, benzene, toluene, naphtha, tetrahydrofuran, diglyme, and aqueous and non-aqueous mixtures thereof, such as acetone and water, acetone and methanol, acetone and ethyl alcohol, methylene dichloride and methanol, and ethylene dichloride and methanol.

DESCRIPTION OF EXAMPLES OF THE INVENTION

The following examples are illustrative of the present invention, and they should not be considered as limiting the scope of the invention in any way, as these examples and other equivalents thereof will become apparent to those versed in the art in light of the present disclosure, drawings and accompanying claims.

EXAMPLE 1

A therapeutic composition comprising a leukotriene-receptor antagonist was prepared as follows: first, a compositional binder solution was prepared by adding 7650 g of purified water into a solution vessel. Next, 1350 g of polyvinylpyrrolidone possessing a viscosity-average molecular weight of 40,000 was added slowly to the vessel, and the solution mixed gently for about 40 minutes to produce a homogenous solution.

Next, a drug composition was prepared as follows: first, 2010 g of tromethamine, (2-amino-2-hydroxymethyl-1, 3-propanediol) was passed through a 20 mesh screen, U.S. Sieve Series. Then, 60 g of colloidal silicon dioxide was passed through a 40 mesh screen. Then, 2400 g of sodium carboxymethylcellulose possessing a viscosity, measured by a Brookfield viscometer, at 25° C., of a 2% concentration between 25–45 cps, a degree of substitution of 0.70–0.80 mol, about 35,000 molecular weight, was placed into a plastic bag. Next, 2280 g of polyvinylpyrrolidone of 40,000 viscosity-average molecular weight was passed through a 40 mesh screen and added to the same plastic bag. Then, the screened colloidal silicon dioxide is added to the same plastic bag and the bag tumbled for 1 minute to obtain a blend of sodium carboxymethylcellulose, polyvinylpyrrolidone and colloidal silicon dioxide.

Next, a fluid bed granulator bowl is heated to 28° C. Then, 4320 g of the leukotriene-receptor antagonist, amorphous zafirlukast was added to the bowl. Next, the 2010 g of tromethamine was added to the granulator bowl, followed by the triblend comprising the sodium carboxymethylcellulose, the polyvinylpyrrolidone and the colloidal silicon dioxide. Then, 6000 g of the binder solution was sprayed into the bowl at a rate of 80–125 ml/min. Then, 3000 g of purified water was added to the granulation bowl. During spraying the air flow was maintained at 50 slpm (standard liters per minute). Also, during the granulation process, the binder solution was sprayed for 40 seconds, followed by shaking for 15 seconds. Next, the granulation was dried to obtain a moisture content of 5.0–7.5%. The granulation was passed through a 8 mesh screen into a laboratory mill. Then, 30 g of magnesium stearate was passed through a 40 mesh screen, added to the blend and blended for 2 minutes. The drug composition is pressed into dosage form tablets, comprising 10 mg, 20 mg, 40 mg, or 80 mg of the leukotriene-receptor antagonist zafirlukast indicated for the prophylaxis and chronic treatment of asthma in adult and children patients.

EXAMPLE 2

A composition possessing expandable kinetics was prepared as follows: first, a binder solution was prepared by adding 9660 g of hydroxypropylmethylcellulose possessing a number-average molecular weight of 13,000 (5 cps) into a mixing vessel containing 133,400 g of purified water. Next, 6900 g of hydroxypropylcellulose possessing a molecular weight of 80,000 was added to the mixing vessel. This mixture was stirred until the ingredients dissolve in the water and to obtain a homogenous solution.

Next, granules for forming an expandable osmotic composition were prepared as follows: first, 36,000 g of osmagent sodium chloride were milled in a grinder and passed through a 21 mesh screen. Also, 600 g of red ferric oxide colorant were milled and passed through a 21 mesh screen. Then, a granulator was heated to 40° C. and 68,400 g of sodium carboxymethylcellulose possessing a viscosity at 25° C. in a 1% concentration of 3,000 to 4,000 cps, a degree of substitution of 0.8 to 0.9 mol. and a molecular weight of 300,000 was placed into the bowl of a granulator. Then, the 36,000 g of milled sodium chloride is added to the granulator followed by 600 g of the colorant red ferric oxide, accompanied by granulation. Next, 30,400 g of the binder solution was sprayed onto the powder bed at a rate of 1100 g/minute, during a processing temperature of 40° C., with constant shaking to dislodge powders from adhering from the granulator. At the end of the process, the moisture content was adjusted to 6.5 to 8.5%. Next, the granulation was screened and placed into a blender, followed by the addition of 586 g of colloidal silicon dioxide screened through a 30 mesh screen. The mixture was blended at 7 rpm for four minutes, to yield an expandable composition.

EXAMPLE 3

A bilayer core was manufactured by compressing into layered arrangement the drug leukotriene-receptor antagonist and the expandable osmotic composition. The drug layer comprising the zafirlukast composition and the expandable-push layer comprising the expandable composition were compressed in a bilayer tablet press fitted with a 9.53 mm round and concave punches and dies. The drug composition was filled into the first hopper attached to the bilayer tablet press, and the expandable composition was filled into the second hopper attached to the bilayer tablet press. The press automatically dispenses 242 mg of the drug composition into a die cavity which is tamped under a force of 80 lbs, (pounds). Next, 155 mg of the expandable composition is added to the die cavity and both the drug layer and the expandable layer are compressed under a force of 1800 lbs. This process produces a thickness of the bilayer core of 5.33 mm and an average hardness of 10 kp (kilopons). The bilayer core produced by this manufacture comprises a drug layer comprising 80 mg of amorphous zafirlukast, 47.4 mg of sodium carboxymethylcellulose, 62 mg of polyvinylpyrrolidone, 39.6 mg of tromethamine, 11 mg of water, 1.3 mg of colloidal silicon dioxide and 0.6 mg of magnesium stearate; the expandable layer comprises 88.4 mg of sodium carboxymethylcellulose, 46.5 mg of sodium chloride, 7.8 mg of hydroxypropylcellulose, 10.8 mg of hydroxypropylmethylcellulose, 0.8 mg of ferric oxide, and 0.8 mg of colloidal silicon dioxide. The bilayer can be administered as a bilayer dosage form to a patient in need of leukotrieneant-agonist therapy, and/or it can be enveloped with a semipermeable wall and administered as a drug delivery device.

EXAMPLE 4

The bilayered core, described immediately above, was coated with a wall comprising a semipermeable composition as follows: A closed, mixing vessel was used to manufacture a mixing solution. The mixing vessel was purged with nitrogen. Then, 47,600 g of acetone was charged to the mixing vessel, and the vessel heated to 25° C. to 30° C. Next, 1 g of Poloxamer® 188, a polyoxyethylene-polyoxypropylene glycol copolymer of the formula $HO(C_2H_4O)_a(C_3H_6O)_b(C_2H_4O_2)_aH$ wherein a equals 80 and b equals 27 having a average molecular weight between 7680 and 9510 was slowly added with stirring to the mixing vessel. Next, the Poloxamer and the acetone are mixed for 10 to 15 minutes. Then, 1979.1 g of cellulose acetate comprising an acetyl content of 39.8% was added to the mixing vessel. Then, the ingredients were mixed for 2 hours to produce a clear solution.

Next, the bilayer cores were coated in a 24-inch perforated pan coater. The coating pan was heated to an exhaust temperature of 40° C. to 45° C. Then, 11,000 g of the bilayer compressed cores were placed into the pan coater. Then, the pan was rotated at 13 rotations per minute. Next, the wall-forming coating solution was sprayed onto the rotating cores at a rate of 110 ml/min from 2 spray guns. During the coating process, the air volume in the coater was maintained between 350 and 370 cfm, cubic feet per minute. The coating process was stopped when the desired amount of semipermeable wall-forming composition was sprayed onto the cores.

Next, a 30 mil (0.76 mm) orifice was drilled through the semipermeable wall on the drug side of the just manufactured dosage forms. Then, the residual acetone was removed by drying at 45° C. and at 45% relative humidity in an oven for 68 hours. At the end of the drying cycle, the humidity was turned off and the dosage forms were dried at 45° C., for an additional 4 hours, to yield the dosage forms.

EXAMPLE 5

The dissolution of the drug zafirlukast indicates the drug entered into solution upon its delivery from a dosage form provided by this invention was measured by the following procedure. First, an aqueous sodium dodecyl sulfate, 1% (wv) (weight/volume) solution was used as the dissolution media. A dosage form prepared by this invention was placed into the dissolution media and the drug released by the dosage form into the dissolution media was sampled at a constant time interval over the time period of dissolution. The filtered samples were assayed by a reversed high pressure liquid chromatography with detection by UV at 224 nm. The concentration of the samples were measured against a standard curve containing at least five standard points. The dissolution test indicates the zafirlukast remains in its amorphous state in the dissolution media. Procedures for dissolution testing are reported in *The United States Pharmacopoeia*, The National Formulary, pg. 1791 to 1796, (1995); *Pharmaceutical Sciences*, by Remington, 17th. Ed., pg. 653 to 666 (1985); and USP XXII, Dissolution Paddle Analysis, pg. 1578–1579 (1990).

The release rate of drug, zafirlukast, from a dosage form manufactured by this invention was ascertained by the following procedure. The procedure comprises placing the dosage form in a solution, usually water, and taking aliquots of the release rate solution, followed by their injection into a chromatographic system to quantify the amount of drug released during specified test intervals. The drug, for example, zafirlukast, was resolved on a column and detected by UV absorption at 224 nm. Quantitation was performed by linear regression analysis of peak areas from a standard curve containing at least five standard points.

Figure 5:
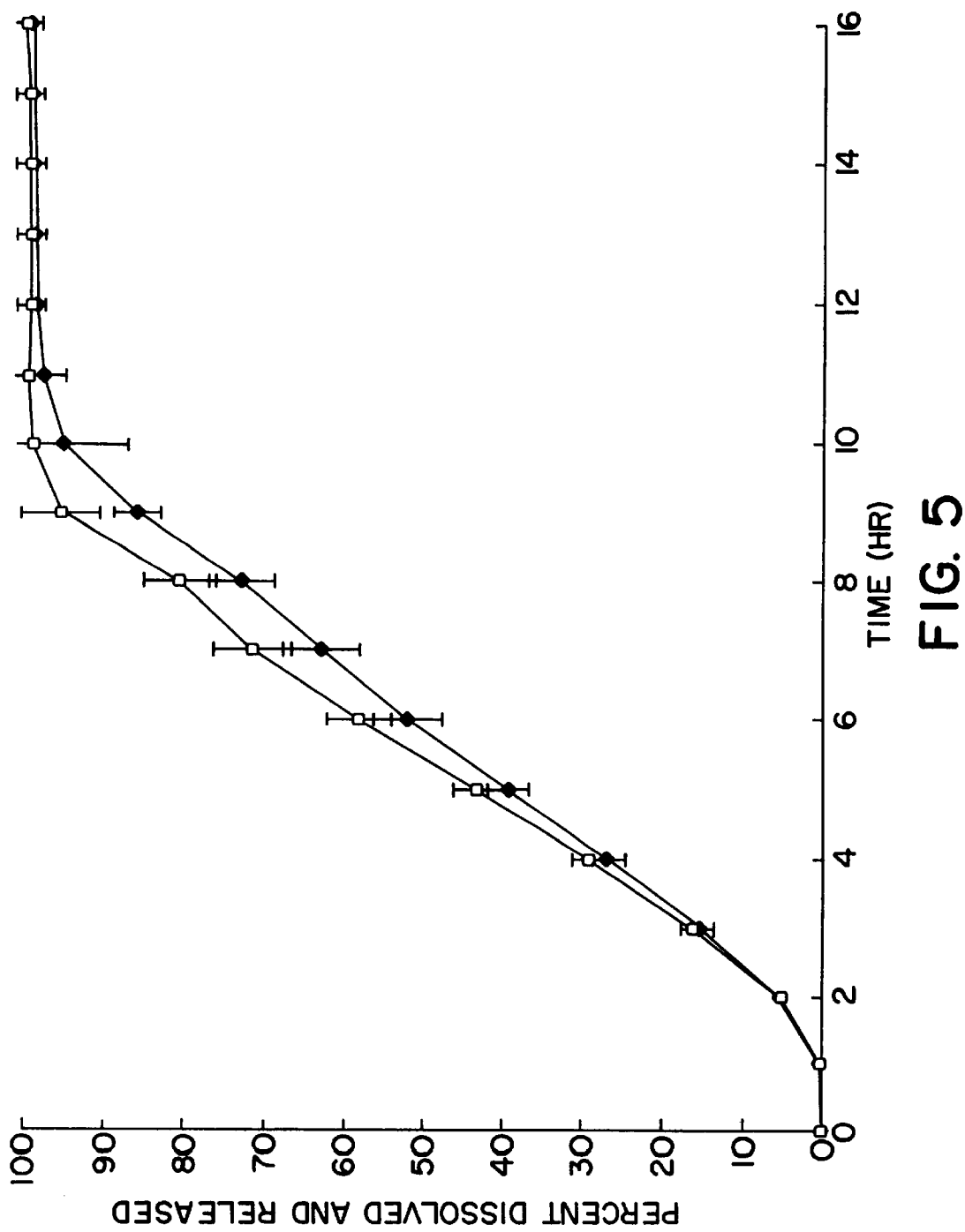
FIGS. 5 to 10 illustrate delivery parameters for delivery system provided by the invention.
Figure 6:
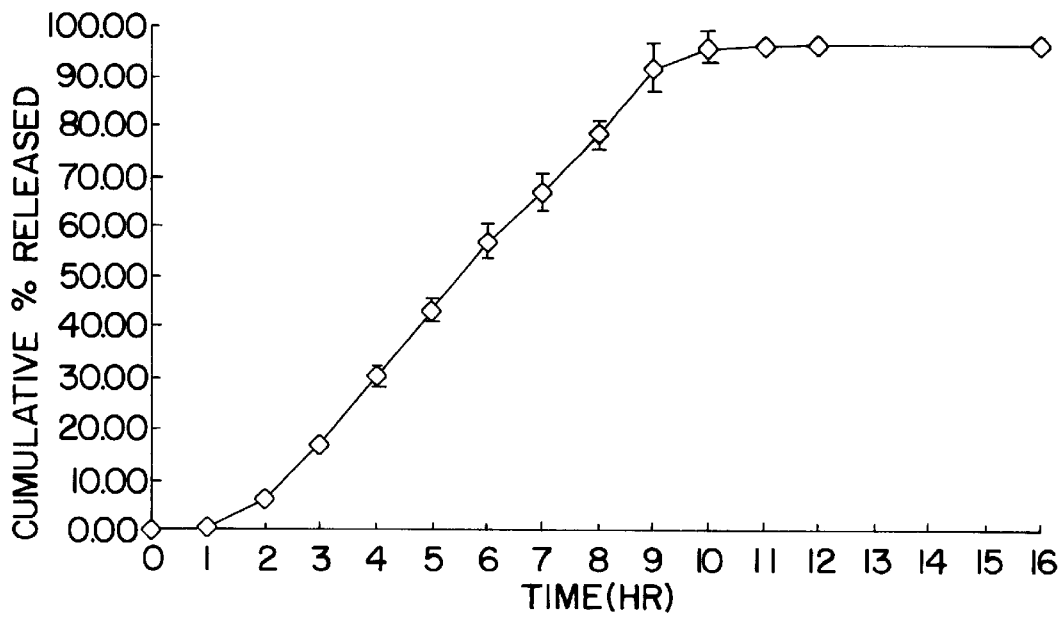
Figure 7:
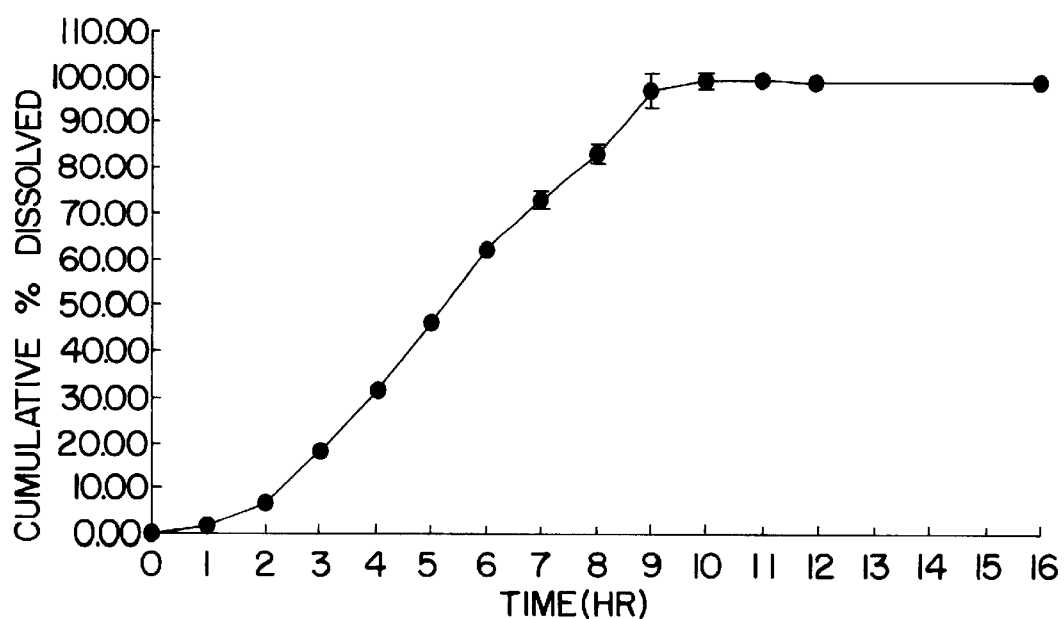

The release rate procedure comprises attaching a dosage form to a plastic rod with the orifice exposed to the drug receiving solution. Then, attaching the rod to a release rate arm, with the arm affixed to an up/down reciprocating shaker, which operates at an amplitude of about 3 cm and 2 seconds per cycle. Then, continuously immersing the dosage form in 50 ml test tubes containing 30 ml of $H_2O$, equilibrated in a constant temperature water bath at 37° C. ±0.5° C. Next, at the end of each interval, transfer the dosage form to the next row of new test tubes containing water. After the release pattern is complete, remove the tubes and allow to cool to room temperature, followed by filling the calibrated tubes to the 50 ml mark with acetone. The samples are mixed immediately, transferred to sample vials, followed by chromatography analysis. The dosage form prepared by the example comprises a drug layer comprising 80 mg of micronized, amorphous zafirlukast, 47.4 mg of sodium carboxymethylcellulose, 62 mg of polyvinylpyrrolidone, 39.6 mg of tromethamine, 11 mg of water, 1.3 mg of colloidal silicon dioxide, and 0.6 mg of magnesium stearate; a push layer comprising 88.4 mg of sodium carboxymethylcellulose, 46.5 mg of sodium chloride, 7.8 mg of hydroxypropylcellulose, 10.8 mg of hydroxypropylmethylcellulose, 0.8 mg of red ferric oxide, and 0.8 mg of colloidal silicon dioxide; a wall comprising 26 mg of cellulose acetate comprising 39.8 acetyl content and 5 mg of surfactant Poloxamer 188; and, a 0.76 mm orifice. Accompanying drawing FIG. 5 illustrates the average cumulative drug dissolved depicted by clear boxes and the average cumulative drug released, depicted by dark diamonds, over an extended period of 16 hours. The graph illustrates zafirlukast is delivered by the dosage form without conversion to a crystalline monohydrate or forms, and the release rate and the dissolution rate are substantially the same. FIG. 6 depicts the cumulative percent of zafirlukast released versus time for the dosage form; and FIG. 7 depicts the cumulative percent dissolved for zafirlukast versus time.

EXAMPLE 6

Figure 8:
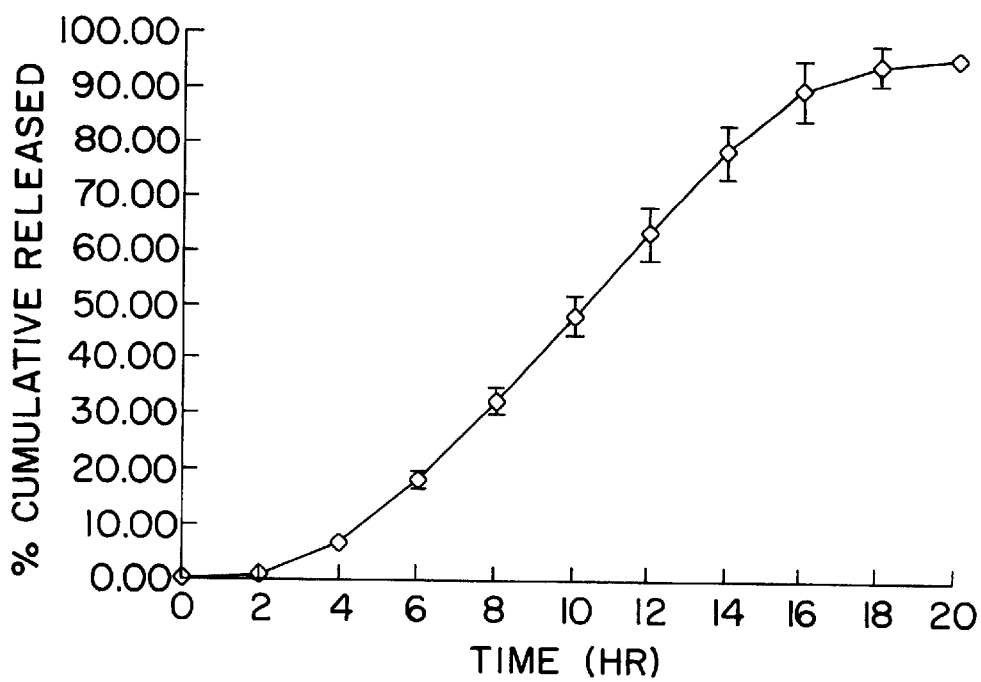
Figure 9:
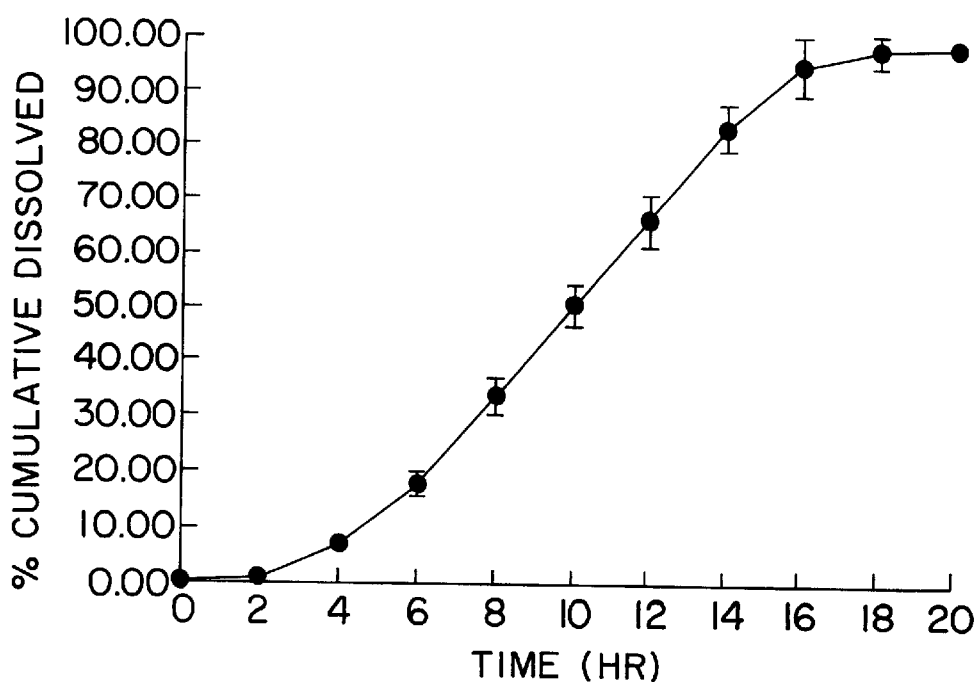

The above procedures are followed with all manufacturing conditions as set-forth, except for the present manufacture the semipermeable wall comprises 85% cellulose acetate with an acetyl content of 39.8% and 15% Poloxamer® 188, a ethylene oxide-propylene oxide-ethylene oxide triblock copolymer available as Pluronic F68 from BASF Corporation, Mt. Olive, N.J. to provide a dosage form comprising the bilayer drug and push layers with a mean release rate of 10.51 mg/hr. Accompanying FIG. 8 depicts the cumulative release rate percent over a time period of 20 hours from the dosage form. Accompanying FIG. 9 depicts the cumulative percent of the drug dissolved versus time on release from a dosage form.

EXAMPLE 7

A dosage form designed and shaped like an osmotic dosage form to deliver the crystalline form of zafirlukast was manufactured as follows: first, a drug layer comprising zafirlukast was made by passing 16.75 g of tromethamine through a 20 mesh screen. Next, 33 g of crystalline zafirlukast was added to a 500 ml beaker, then 20 g of polyvinylpyrrolidone with an average molecular weight of 40,000 was added to the beaker. Next, 30 g of carboxymethylcellulose sodium, having an average molecular weight of 35,000 is added to the beaker. Next, all the ingredients were mixed with a spatula and 60 ml of denatured anhydrous ethanol was added to the beaker with mixing to change the consistency of the dry powder ingredients to granules. The granulation then was placed in a hood overnight to dry. The dried granules were passed through a 20 mesh screen to obtain a consistency in granule size. Next, the granulation is transferred to a glass jar, 0.25 g of magnesium stearate added thereto, and the granulation mixed on rollers to produce a zarfirlukast drug composition for processing into a drug layer.

An expandable-push layer was prepared by following the expandable-push procedure described above.

Next, a tablet press was used to compress the two layers in bilayered arrangement to form a tablet. First, 260 mg of the drug layer provided immediately above was added to a 10.32 mm die cavity and lightly tamped to yield the drug layer. Next, 140 mg of the expandable-push layer was placed in the same cavity and the two layers compressed under 1 ton of pressure to form a bilayer tablet.

Next, the bilayered tablet was surrounded with a wall comprising a semipermeable polymeric composition by following the procedures set-forth above. The wall-forming composition comprises 100% cellulose acetate possessing an acetyl content of 32.0%. The wall-forming composition was dissolved in a mixture of acetone and water to provide a cosolvent ratio of 88:12 (v:v), with a solid composition of 5%.

Figure 10:
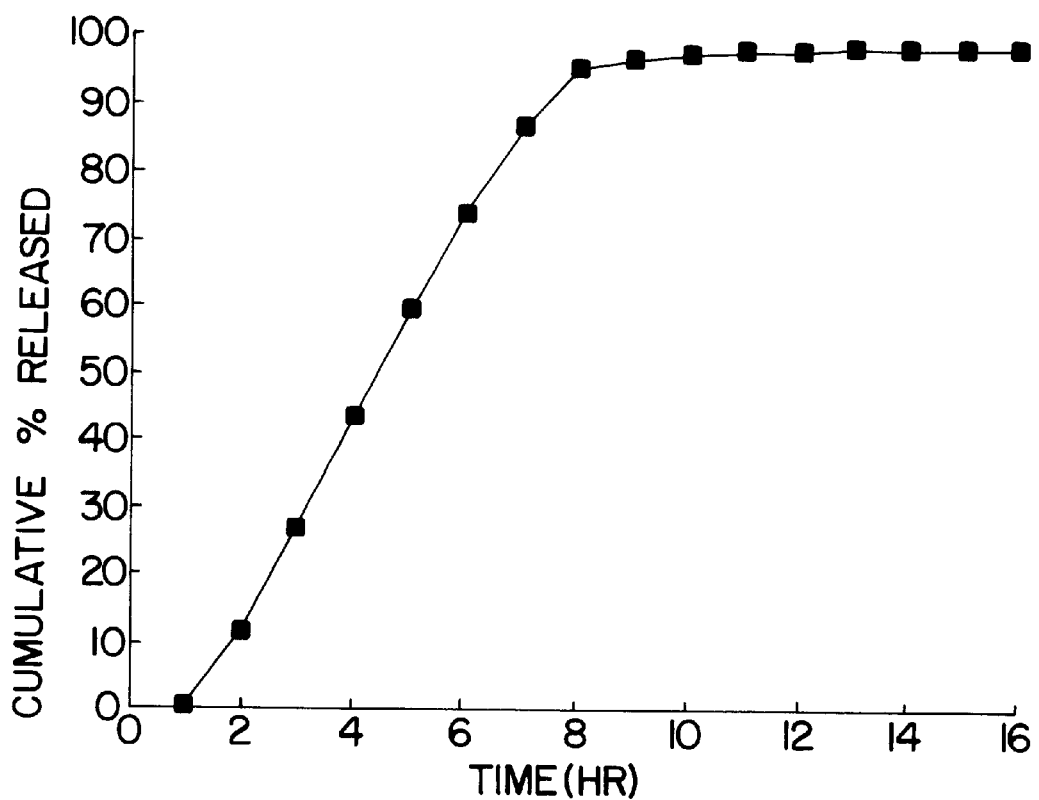

The dosage form provided by this example exhibited an average release rate of 12 mg/hr for 16 hours. The percent cumulative zafirlukast (crystalline) released for this osmotic dosage form is depicted in drawing FIG. 10. The dosage form comprised a 0.76 mm drug-releasing orifice.

EXAMPLE 8

A dosage form tablet designed and shaped for oral administration to an asthmatic patient in need of leukotriene-receptor antagonist therapy is manufactured as follows: first, 16.75 g of tromethamine is passed through a 20 mesh screen. Then, 33 g of a leukotriene-receptor antagonist selected from the group consisting of acitazanolast, iralukast, montelukast, praniukast, verlukast, zafirlukast, and zileuton is added to a beaker, followed by adding 20 g of polyvinylpyrrolidone to the beaker, possessing a average molecular weight of 40,000. Then, 5.2 g of osmagent sodium chloride is added to the beaker with mixing to produce a homogenous mass. Next, 30 g of osmagel polyethylene oxide possessing a 100,000 molecular weight is added to the beaker and all the ingredients mixed in the presence of anhydrous ethanol, to form granules. The granules are dried at 25° C. for 12 hours and then passed through a 20 mesh screen. Next, the granules are transferred to a glass jar, and, 0.25 g of magnesium stearate is added thereto, and the granules mixed to produce a therapeutic composition comprising a leukotriene-receptor antagonist.

Next, 260 mg of the therapeutic composition is added to a tablet press and compressed under a pressure of 1½ tons to a tablet core. Then, the tablet core is enveloped with a wall composition comprising 90% cellulose acetate having an acetyl content of 32% and 10% polyethylene glycol having a molecular weight of 3,350 dissolved in a solvent. The solvent comprises acetone and water, 88:12, wt:wt, to effect a solid composition of the solution of 5%. The coating temperature is 35° C. to apply the semipermeable wall around the drug core. Next, a 50 mil (1.27 mm) passageway is drilled through the semipermeable wall and the residual solvent is removed by drying at 45° C. and 45% relative humidity in an oven for 48 hours. At the end of the drying, the humidity is turned off, and the dosage form dried at 45° C. for an additional 4 hours to provide an osmotic dosage form for orally administering the leukotriene-antagonist to a patient suffering with the symptoms of asthma.

EXAMPLE 9

A drug composition comprising a drug selected from the group consisting of acitazanolast, iralukast, montelukast, praniukast, verlukast, zafirlukast, and zileuton is prepared as follows: first, 2,580 g of polyethylene oxide having a weight-average molecular weight of 200,000 is passed through a 40 mesh screen. Then, 1,290 g of the screened polyethylene oxide is placed into the bowl of a mixer. Then, 2,400 g of a drug listed above is placed in the mixer over the polyethylene oxide. Next, 300 g of polyvinylpyrrolidone of 40,000 viscosity-average molecular weight is passed through a 40-mesh screen and added to the mixer. The remaining 1,290 g of polyethylene oxide then is added to the bowl. Next, 300 g of sorbitol and 360 g of tromethamine (2-amino-2-hydroxymethyl-1, 3-propanediol) is passed through a 40 mesh screen and added to the mixer. The addition of the dry ingredients is performed with the drug located between the two layers of polyethylene oxide. The granulation process is initiated by the gradual addition of 3,200 g of ethyl alcohol with continuous mixing to the mixer. Mixing is continued over a period of 5 to 10 minutes to effect a consistency to change the dry powder to granules. The wet granulation is dried at 40° C. for 16 hours and then passed through a fluid air mill with a 7-mesh screen for size reduction. Next, the sizereduced granules are placed into a binder. Then, 60 g of magnesium stearate that is passed through a 60-mesh screen is added to the granulation, and all the ingredients mixed for 4 minutes. This composition provides a leukotriene-receptor antagonist, polyethylene oxide, polyvinylpyrrolidone, tromethamine, sorbitol, and magnesium stearate, useful for the management of asthma.

Next, a composition possessing expandable kinetics is prepared as follows: first, a binder solution is prepared by adding 300 g of polyvinylpyrrolidone of 40,000 average-molecular weight to a mixer containing 2,700 g of water. Then, the mixture is stirred until the polyvinylpyrrolidone dissolves in the water and forms a clear binder solution.

Next, the granules for forming an expandable, osmotic composition are prepared as follows: first, 7,370 g of polyethylene oxide having an average-molecular weight of 7,000,000 is placed into the bowl of a fluid bed granulator. Then, 200 g of polyvinylpyrrolidone possessing an average-molecular weight of 40,000 is added to the granulator. Next, 2,000 g of sodium chloride and 100 g of red ferric oxide, which was milled using a 20-mesh screen are added to the granulator. The powder ingredients are fluidized for 3 minutes to produce a uniform mixing of the powders. Next, the binder solution is sprayed onto the powders at a solution spray rate of 50 g/min. During the spraying process the process air flow is maintained at 500 cfm and the temperature maintained at 24° C. During the spraying operation the solution is sprayed for 30 seconds, followed by a shaking time of 10 seconds. At the end of the spraying operation, the granules are dried in the granulator for an additional 10 to 15 minutes to obtain a dry granulation. The granules are passed through a fluid air mill with a 7-mesh screen for size reduction. The size reduced granules then are placed into a blender. Then, 25 g of magnesium stearate, previously screened through a 40-mesh screen, and 5 g of powdered butylated hydroxytoluene, previously screened through a 60-mesh screen, are added to the granules and mixed together to provide an osmotically expandable composition.

Next, a bilayered core is manufactured by compressing in layered arrangement the drug composition and the osmotic, expandable composition described above as follows: first, 750 mg of the leukotriene-receptor antagonist composition is added into the cavity of a 5/16-in. (8-mm) diameter, and then 300 mg of the osmotic expandable composition is placed into the die and the two compositions compressed into layered arrangement with 1 ton (2,000 lb.) of pressure.

Next, a wall forming composition comprising 90% cellulose acetate having an acetyl content of 32% and 10% polyethylene glycol having a molecular weight of 3,350 is dissolved in a solvent. The solvent comprises acetone and water, 88:12, wt:wt, to effect a solid composition of the solution of 5%. Then, the bilayer cores are placed into a 12-inch (30-cm) coating pan and the coating solution is sprayed onto the bilayer cores at a spray rate of 25 g/min. The coating temperature is 35° C. to apply 140 mg of the semipermeable wall around and in contact with the bilayer core.

Next, a 50-mil (1.27 mm) passageway is drilled through the semipermeable wall into the drug side of the dosage form. The residual solvent is removed by drying at 45° C. and 45% relative humidity in an oven for 48 hours. At the end of the drying, the humidity is turned off and the dosage forms are dried at 45° C. for an additional 4 hours, to provide an osmotic dosage form for orally administering a leukotriene-receptor antagonist to a patient suffering with the symptoms of asthma.

METHOD OF USING THE INVENTION FOR ANTI-ASTHMA THERAPY

A special embodiment of the invention pertains to a method for administering a leukotriene-receptor antagonist to a patient in need of antiasthma therapy. The invention comprises a method of (1) administering orally a dosage form tablet comprising a leukotriene-receptor antagonist; (2) administering a dosage form composition comprising a leukotriene-receptor antagonist surrounded by a wall comprising an exit passageway; (3) administering a dosage form comprising a leukotriene-receptor antagonist composition in contacting arrangement with an expandable-push composition with both compositions surrounded by a wall with a passageway; (4) administering a dosage form composition comprising a leukotriene-receptor antagonist surrounded by a wall with a passageway and a leukotriene-receptor antagonist overcoat on the exterior of the dosage form; and (5) administering a dosage form comprising a leukotriene-receptor antagonist composition in contacting arrangement with an expandable-push composition with both compositions surrounded by a wall with a passageway and a leukotriene-receptor antagonist on the exterior surface of the wall, for antiasthma therapy.

In summary, it will be appreciated the present invention contributes to the antiasthma art an unobvious dosage form that possess a practical utility, can administer an antiasthma drug in a prompt dose and in a known dose released per unit time over time. While the invention has been described and pointed out in detail with reference to operative embodiments thereof, it will be understood to those skilled in the antiasthma art that various changes, modifications, substitutions and omissions can be made without departing from the spirit of the invention. It is intended, therefore, that the invention embrace those equivalents within the scope of the claims which follow.

What is claimed is:

1. A dosage form comprising 2 milligrams to 500 milligrams of a leukotriene-receptor antagonist in a dosage form selected from the group consisting of an amorphous form, a crystalline monohydrate form, and a crystalline anhydrous form, and 20 milligrams to 300 milligrams of a pharmaceutically acceptable carboxyalkylcellulose carrier wherein the dosage form is substantially-free from conversion to a different dosage form.

2. The dosage form according to claim 1, wherein the leukotriene-receptor antagonist is selected from the group consisting of acitazanolast, iralukast, montelukast, pranlukast, velukast, zafirlukast, and zileuton.

3. The dosage form of claim 1, wherein the dosage form is an amorphous dosage form.

4. The dosage form according to claim 3, wherein the leukotriene-receptor antagonist is selected from the group consisting of acitazanolast, iralukast, montelukast, pranlukast, velukast, zafirlukast, and zileuton.

5. A dosage form comprising 2 milligrams to 500 milligrams of a leukotriene-receptor antagonist in a dosage form selected from the group consisting of an amorphous form, a crystalline monohydrate form, and a crystalline anhydrous form, and 20 milligrms to 300 milligrams of a pharmaceutically acceptable polyalkylene oxide carrier wherein the dosage form is substantially-free from conversion to a different dosage form.

6. The dosage form according to claim 5, wherein the leukotriene-receptor antagonist is selected from the group consisting of acitazanolast, iralukast, montelukast, pranlukast, velukast, zafirlukast, and zileuton.

7. A dosage form for delivering a leukotriene-receptor antagonist to a patient in need of leukotriene-receptor antagonist therapy, wherein the dosage form comprises:
   (a) a wall permeable to fluid and impermeable to a leukotriene-receptor antagonist, which wall surrounds;
   (b) a drug formulation comprising a leukotriene-receptor antagonist in a dosage form selected from the group consisting of an amorphous form, a crystalline monohydrate form, and a crystalline anhydrous form, and a pharmaceutically acceptable carrier means for assisting the dosage form in delivering the leukotriene-receptor antagonist wherein the dosage form is substantially-free from conversion to a different dosage form; and
   (c) an exit in the wall for delivering the leukotriene-receptor antagonist from the dosage form.

8. The dosage form according to claim 7, wherein the leukotriene-receptor antagonist is coated on the exterior of the dosage form.

9. The dosage form according to claim 7, wherein the pharmaceutically acceptable carrier is polyethylene oxide.

10. The dosage from according to claim 7, wherein the pharmaceutically acceptable carrier is a carboxyalkylcellulose.

11. The dosage form according to claim 7, wherein the drug formulation comprises an osmagent.

12. A dosage form for delivering a leukotriene-receptor antagonist to an environment of use, wherein the dosage form comprises:

(a) a wall that surrounds;

(b) a drug formulation comprising a leukotriene-receptor antagonist in a dosage form selected from the group consisting of an amorphous form, a crystalline monohydrate form, and a crystalline anhydrous form, and a pharmaceutically acceptable carrier means for transporting the leukotriene-receptor antagonist from the dosage form wherein the dosage form is substantially-free from conversion to a different dosage form;

(c) an expandable-push composition in contact with the drug formulation that provides a continuous push for assisting in delivering the leukotriene-receptor antagonist from the dosage form; and, (d) an exit in the wall for delivering the leukotriene-receptor antagonist from the dosage form.

13. The dosage form according to claim 12 wherein the leukotriene-receptor antagonist is selected from the group consisting of acitazanolast, iralukast, montelukast, pranlukast, velukast, and zileuton.

14. The dosage form according to claim 12, wherein the leukotriene-receptor antagonist is zafirlukast.

15. The dosage form according to claim 12, wherein the pharmaceutically acceptable carrier is a carboxyalkylcellulose.

16. The dosage form according to claim 12, wherein the expandable-push composition comprises a catboxyalkylcellulose possessing a higher molecular weight than the pharmaceutically acceptable carrier carboxyalkylcelluose.

17. The dosage form according to claim 12, wherein the pharmaceutically acceptable carrier is a polyalkylene oxide.

18. The dosage form according to claim 12, wherein the expandable-push composition comprises a polyalkylene oxide that possess a higher molecular weight than the pharmaceutically acceptable carrier polyalkylene oxide.

19. A method for decreasing the frequency of administering a dose of zafirlukast to a patient while maintaining the therapeutic effect of the zafirlukast, wherein the method comprises administering orally to the patient a dosage form that administers a sustained-release dose of zafirlukast over twenty-four hours and thereby decreases the frequency of dosing and maintains the therapeutic effect of the zafirlukast.

20. A method for producing a plasma concentration of zafirlukast in a patient, wherein the method comprises administering orally to the patient a dosage form that delivers a sustained-release dose of zafirlukast over a therapeutic time to produce a plasma concentration of zafirlukast proportional to the delivered dose of zafirlukast over the therapeutic time.

21. A method of delivering a leukotriene-receptor antagonist to a fluid environment of use, wherein the method comprises admitting into the fluid environment a dosage form possessing a leukotriene-receptor antagonist release rate that corresponds to the leukotriene-receptor antagonist dissolution rate in the fluid over time.

22. A method of delivering zafirlukast to a fluid environment of use, wherein the method comprises delivering zafirlukast at a controlled-sustained release rate to the fluid environment.

23. A method of delivering a leukotriene-antagonist in a dosage form selected from the group consisting of an amorphous form, a crystalline monohydrate form, and a crystalline anhydrous form wherein the method comprises providing the dosage form in a dosage form substantially-free from conversion to a different dosage form.

24. The method according to claim 23, wherein the method comprises blending a leukotriene-antagonist with a buffering agent, a binder and a pharmaceutically acceptable carrier that provide a composition that maintains the leukotriene-antagonist in the initial dosage form.

25. The method according to claim 23, wherein the composition is surrounded by a wall comprising a polymer.

* * * * *